(12) United States Patent
Goldman et al.

(10) Patent No.: US 11,291,984 B2
(45) Date of Patent: Apr. 5, 2022

(54) DEHYDROGENATION OF SUBSTRATES BY TRANSITION METAL COMPLEXES

(71) Applicants: Rutgers, The State University of New Jersey, New Brunswick, NJ (US); ExxonMobil Research and Engineering Company, Annandale, NJ (US)

(72) Inventors: Alan S. Goldman, Piscataway, NJ (US); Santanu Malakar, Piscataway, NJ (US); Xiaoguang Zhou, Piscataway, NJ (US); Kun Wang, Bridgewater, NJ (US); David O. Marler, Easton, PA (US)

(73) Assignees: Rutgers, The State University of New Jersey, New Brunswick, NJ (US); ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 17/209,816

(22) Filed: Mar. 23, 2021

(65) Prior Publication Data
US 2021/0291154 A1    Sep. 23, 2021

Related U.S. Application Data

(60) Provisional application No. 62/993,145, filed on Mar. 23, 2020.

(51) Int. Cl.
| | | |
|---|---|---|
| *B01J 31/22* | (2006.01) | |
| *C07F 15/00* | (2006.01) | |
| *C07C 2/26* | (2006.01) | |
| *C07C 5/333* | (2006.01) | |

(52) U.S. Cl.
CPC .............. *B01J 31/2273* (2013.01); *C07C 2/26* (2013.01); *C07C 5/333* (2013.01); *C07F 15/0033* (2013.01); *C07C 2531/22* (2013.01)

(58) Field of Classification Search
CPC ........ B01J 31/2273; C07C 5/333; C07C 2/26; C07C 2531/22; C07F 15/0033
See application file for complete search history.

(56) References Cited

U.S. PATENT DOCUMENTS

| | | | |
|---|---|---|---|
| 11,020,731 B2 | 6/2021 | Goldman et al. | |
| 2013/0317212 A1* | 11/2013 | Nazeeruddin | H01L 51/0085 540/541 |

FOREIGN PATENT DOCUMENTS

WO      2013130972 A1     9/2013

OTHER PUBLICATIONS

Allen et al. ("Regeneration of an Iridium(III) Complex Active for Alkane Dehydrogenation Using Molecular Oxygen", Organometallics 2014, 33, 1337-1340) (Year: 2014).*
Pahls et al. ("Understanding the Effect of Ancillary Ligands on Concerted Metalation-Deprotonation by (dmPhebox)Ir(OAc)2(H2O) Complexes: A DFT Study", Organometallics 2014, 33, 6413-6419) (Year: 2014).*
Ito et al. ("Intermolecular C—H Bond Activation of Alkanes and Arenes by NCN Pincer Iridium(III) Acetate Complexes Containing Bis (oxazolinyl)phenyl Ligands", Organometallics 2012, 31,4442-4449) (Year: 2012).*
Yuan et al. ("Effect of Carboxylate Ligands on Alkane Dehydrogenation with (dmPhebox)Ir Complexes", ACS Catal. 2018, 8, 2326-2329) (Year: 2018).*
Nückel et al. (Transition Metal Complexes with Sterically Demanding Ligands, 3.1 Synthetic Access to Square-Planar Terdentate Pyridine-Diimine Rhodium(I) and Iridium(I) Methyl Complexes: Successful Detour via Reactive Triflate and Methoxide Complexes, Organometallics 2001, 20, 4345-4359) (Year: 2001).*
Adams, et al., "Investigation of CF3 Iridium PCP Pincer Catalytic Dehydrogenation and Decarbonylation Chemistry", Organometallics, vol. 31, No. 4, 2012, pp. 1439-1447.
Gao, et al., "Iridium-catalyzed dehydrogenative coupling of ethylene to form 1,3-butadiene", Rutgers University 2017 Central Regional Meeting (CERM) presentation. Jun. 8, 2017.
Gao, et al., "β-Hydride Elimination and C-H Activation by an Iridium Acetate Complex, Catalyzed by Lewis Acids. Alkane Dehydrogenation Cocatalyzed by Lewis Acids and [2,6-Bis(4,4-dimethyloxazolinyl)-3,5-dimethylphenyl]iridium", J. Am. Chem. Soc. 2017, 139, pp. 6338-6350.
Ito, et al., "Efficient Preparation of New Rhodium- and Iridium-[Bis(oxazo-linyl)-3,5-dimethylphenyl] Complexes by C-H Bond Activation: Applications in Asymmetric Synthesis", Adv. Synth. Catal. 2006, 348, pp. 1235-1240.
Motoyama, et al., "Bis(oxazolinyl)phenylrhodium(III) Aqua Complexes: Synthesis, Structure, Enantioselective Allylation of Aldehydes, and Mechanistic Studies", Organometallics, vol. 28, No. 8, Mar. 22, 2001, pp. 1580-1591.
Motoyama, et al., "Chiral bis(oxazolinyl)phenylrhodium(III) complexes as Lewis acid catalysts for enantioselective allylation of aldehydes", Chem Comm (Cambridge), Issue 2, 1999, pp. 131-132.
Motoyama, et al., "Novel Asymmetric Michael Addition of alpha-Cyanopropionates to Acrolein by the Use of a Bis oxazolinyl)phenylstannane-Derived Rhodium(III) Complex as a Chiral Lewis Acid Catalyst", Chem Eur J, vol. 8, No. 13, Jun. 24, 2002, pp. 2968-2975.
Motoyama, et al., "Synthesis and X-ray Crystal Structures of Bis(oxazolinyl)phenyl-Derived Chiral Palladium(II) and Platinum(II) and -(IV) Complexes and Their Use in the Catalytic Asymmetric Aldol-Type Condensation of Isocyanides and Aldehydes", Organometallics, vol. 21, No. 16, Jul. 3, 2002, pp. 3408-3416.
Nishiyama, et al., "High Performance of Rh(Phebox) Catalysts in Asymmetric Reductive Aldol Reaction: High Anti-Selectivity", J Am Chem Soc, vol. 127, No. 19, Apr. 26, 2005, pp. 6972-6973.
Nishiyama, H., "Synthesis and use of bisoxazolinyl-phenyl pincers", Chem Soc Rev, vol. 36, No. 7, Jul. 2007, pp. 1133-1141.

(Continued)

*Primary Examiner* — Ali Z Fadhel
(74) *Attorney, Agent, or Firm* — Saul Ewing Arnstein & Lehr LLP; Domingos J. Silva

(57) ABSTRACT

Provided herein are transition metal complexes that are useful in the acceptorless dehydrogenation of various substrates, including alkanes. Also provided are methods of dehydrogenating substrates to provide unsaturated products such as olefins.

27 Claims, 1 Drawing Sheet

(56) References Cited

OTHER PUBLICATIONS

Nobbs, et al., "Thio-Pybox and Thio-Phebox complexes of chromium, iron, cobalt and nickel and their application in athylene and butadiene polymerisation catalysis.", Dalton Trans., 2012, 41, pp. 5949-5964.

Ohshima, et al., "C1-Symmetric Rh/Phebox-Catalyzed Asymmetric Alkynylation of alpha-Ketoesters", Angew Chem Int Ed, vol. 50, 2011, pp. 6296-6300.

Takemoto, et al., "Highly efficient Suzuki-Miyaura coupling reactions catalyzed by bis(oxazolinyl)henyl-Pd(II) complex". Tetrahedron Lett, vol. 48, No. 19, May 7, 2007, pp. 3397-3401.

Zhou, "Computational Study of Pincer Iridium Catalytic Systems: C-H, N-H, and C-C Bond Activation and C-C Coupling Reactions.", A dissertation submitted to the Graduate School-New Brunswick Rutgers, The State University of New Jersey, May 2017.

\* cited by examiner

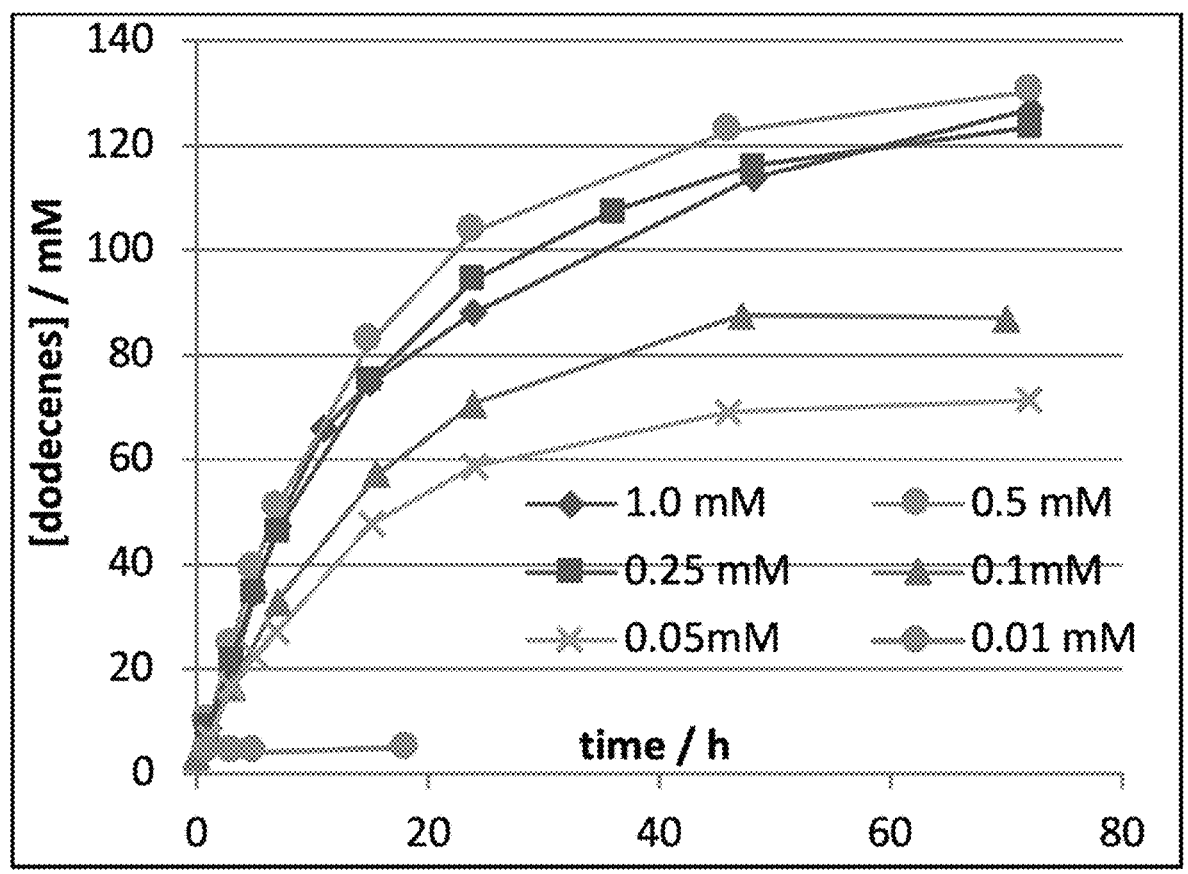

DEHYDROGENATION OF SUBSTRATES BY TRANSITION METAL COMPLEXES

CROSS-REFERENCE TO RELATED APPLICATIONS

This application claims priority under 35 U.S.C. § 119(e) to U.S. Provisional Patent Application No. 62/993,145, filed Mar. 23, 2020, the contents of which are incorporated by reference herein in their entirety.

BACKGROUND

Olefins are among the most versatile intermediates. Their uses range from fine chemicals to manufacture of commodity chemicals and fuels. In comparison, alkanes have little value as direct chemical precursors and in many cases (especially low molecular-weight alkanes) are not even desirable as fuels. The preparation of high-value olefins from abundant cheap alkanes is thus very attractive. Acceptorless dehydrogenation of alkanes is a highly desirable process for producing olefins from alkanes, because no added reagents are required and hydrogen gas ($H_2$) is produced as a valuable byproduct.

There is thus a need in the art for novel compounds and methods for obtaining unsaturated compounds such as olefins from substrates that can be dehydrogenated. The present disclosure addresses this need.

BRIEF SUMMARY OF THE INVENTION

The present disclosure provides transition metal complexes of formula I:

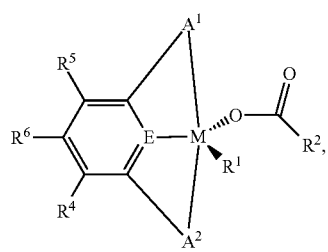

(I)

that are useful in the acceptorless dehydrogenation of various substrates, including alkanes. In certain embodiments, the transition metal (M) is selected from the group consisting of Co, Rh, Ru, and Ir. In certain embodiments, the transition metal (M) is Ir.

The present disclosure further provides methods of dehydrogenating substrates, using the transition metal complexes described herein, to provide unsaturated products such as olefins. In certain embodiments, the dehydrogenation methods described herein are used in a tandem process with an olefin oligomerization reaction to provide a final product which is at least one selected from the group consisting of a heavier olefin, jet or diesel fuel, lubricant basestock, fiber, plastic, and resins.

BRIEF DESCRIPTION OF THE FIGURES

The drawings illustrate generally, by way of example, but not by way of limitation, various embodiments of the present application.

FIG. 1 shows the progress of dehydrogenation of n-dodecane by a catalyst of Formula II ($R^1$=H; $R^3$=$R^{3'}$=$CH_3$; $R^4$=$R^5$=$CF_3$; $R^2$=$CH_3$) under various catalyst loadings.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$) hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$) =CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]

thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypentyl, epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2-(4-methyl-3,4-epoxycyciohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl ($C_1$), ethyl ($C_2$), propyl ($C_3$), or butyl ($C_4$), and $(C_0-C_b)$hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "atm" as used herein refers to a pressure in atmospheres under standard conditions. Thus, 1 atm is a pressure of 101 kPa, 2 atm is a pressure of 202 kPa, and so on.

The term "NaBArF" refers to sodium tetrakis[(3,5-trifluoromethyl)phenyl]borate.

The term "COD" refers to 1,5-cyclooctadiene.

The term "aluminosilicate" as used herein refers to a mineral composition comprising aluminum, silicon, and oxygen. In certain embodiments, the aluminosilicate further comprises a countercation. Non-limiting examples of aluminosilicates include andalusite, kyanite, and sillimanite, each having a molecular formula of $Al_2SiO_5$.

The term "oligomerization" as used herein refers to a chemical process whereby monomeric species are converted to a polymeric species via a finite polymerization process. The monomeric species may be identical or different, resulting in homo-oligomeric or hetero-oligomeric species, respectively.

Preparation of Compounds

Compounds of Formula I or otherwise described herein can be prepared by the general schemes described herein, using the synthetic method known by those skilled in the art. The following examples illustrate non-limiting embodiments of the compound(s) described herein and their preparation. Compounds of Formula I can be prepared by reacting the corresponding ligand with (COD)M(OAc) at elevated temperatures, as further detailed in the Examples.

In one embodiment, a compound of Formula I is provided. The compound of Formula I has the structure:

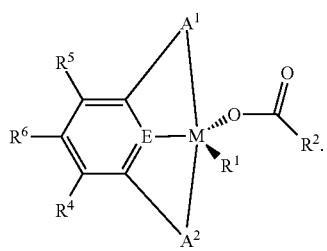

Formula I

In the compound of Formula I,

M is a transition metal;

E is C or N;

$R^1$ is H or $C_{1-16}$ alkyl;

$R^2$ is selected from the group consisting of $CH_{3-m}X_m$, $CF_2CF_3$, $C_{6-14}$ aryl, and $C_{1-16}$ alkyl, wherein the $C_{6-14}$ aryl and $C_{1-16}$ alkyl are each optionally substituted by at least one substituent independently selected from the group consisting of F, Cl, Br, I, OR, OC(O)N(R)$_2$, CN, NO, NO$_2$, ONO$_2$, azido, CF$_3$, OCF$_3$, R, C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O) OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N (R)$_2$, N(R)C(S)N(R)$_2$, N(COR)COR, N(OR)R, C(=NH)N(R)$_2$, C(O)N(OR)R, and C(=NOR)R;

wherein R is independently at each occurrence H or $C_{1-16}$ hydrocarbyl;

each occurrence of X is independently selected from the group of H, F, Cl, and Br;

$A^1$ and $A^2$ are independently moieties that each comprise at least one nitrogen atom coordinated to M;

$R^4$ is selected from the group consisting of CF$_3$, CF$_2$CF$_3$, CN, and NO$_2$;

$R^5$ is selected from the group consisting of CF$_3$, CF$_2$CF$_3$, CN, and NO$_2$;

$R^6$ is independently selected from the group consisting of H, CF$_3$, CF$_2$CF$_3$, CN, and NO$_2$; and each occurrence of m is independently 0, 1, 2, or 3.

In various embodiments, in the compound of Formula I, R is independently at each occurrence H or $C_{1-16}$ alkyl.

In various embodiments, in the compound of Formula I, $R^2$ is selected from the group consisting of $CH_{3-m}X_m$, $CF_2CF_3$, $C_{6-14}$ aryl, and $C_{1-16}$ alkyl, wherein the $C_{6-14}$ aryl and $C_{1-16}$ alkyl are each optionally substituted by at least one substituent independently selected from the group consisting of F, Cl, Br, I, OR, OC(O)N(R)$_2$, CN, NO, NO$_2$, ONO$_2$, CF$_3$, OCF$_3$, R, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O) R, and C(O)N(R)$_2$.

Moieties $A^1$ and $A^2$ can be linear or cyclic, provided they contain at least one nitrogen atom capable of coordinating to metal M. Moieties $A^1$ and $A^2$ can each independently contain from 2 to 100 atoms of B, C, N, O, S, F, Cl, Br, or P, along with the requisite number of hydrogen atoms to satisfy open valences. In the compound of Formula I, the ligand O—C(=O)R$^2$ is depicted as being monodentate, however O—C(=O)R$^2$ can, in some embodiments, coordinate to metal M in a bidentate fashion through both of the oxygen atoms in O—C(=O)R$^2$, as shown in the compound of Formula II.

In some embodiments, the compound has the structure of Formula II:

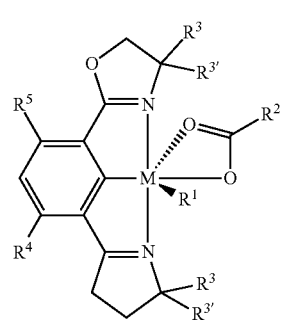

Formula II wherein $R^3$ and $R^{3'}$ are each CH$_3$, or $R^3$ and $R^{3'}$ taken together are —(CH$_2$)$_4$— or —(CH$_2$)$_5$—.

Metal M can be any transition metal, including Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, or Hg. In certain embodiments, M is Co. In certain embodiments, M is Rh. In certain embodiments, M is Ru. In certain embodiments, M is Ir.

In certain embodiments, $R^1$ is H.

In certain embodiments, $R^2$ is CF$_3$. In certain embodiments, $R^2$ is CH$_3$. In certain embodiments, $R^2$ is

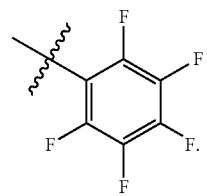 [SMILES: *c1c(F)c(F)c(F)c(F)c1F]

In certain embodiments, $R^2$ is

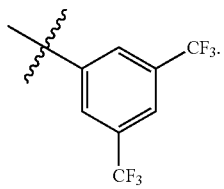 [SMILES: *c1cc(C(F)(F)F)cc(C(F)(F)F)c1]

In certain embodiments, $R^3$ is $CH_3$. In certain embodiments, $R^{3'}$ is $CH_3$. In certain embodiments $R^3$ and $R^{3'}$ are identical.

In certain embodiments, $R^4$ is $CF_3$. In certain embodiments, $R^5$ is $CF_3$. In certain embodiments, $R^4$ and $R^5$ are identical.

Methods of Dehydrogenating Substrates

In various embodiments, a method of dehydrogenating a substrate is provided. The method includes contacting at least one substrate comprising at least one —$CHR^7CHR^8$— group, at least one —$CHR^7CHR^8$—$CHR^9$—OH group, at least one —$CHR^7$—$NHR^8$ group, or a mixture thereof with the compound of Formula I; and forming a corresponding dehydrogenated product from the substrate, wherein $R^7$, $R^8$, and $R^9$ are each independently selected from the group consisting of H, F, Cl, Br, I, OR, $OC(O)N(R)_2$, CN, NO, $NO_2$, $ONO_2$, azido, $CF_3$, $OCF_3$, R, C(O), S(O), methylenedioxy, ethylenedioxy, $N(R)_2$, SR, SOR, $SO_2R$, $SO_2N(R)_2$, $SO_3R$, C(O)R, C(O)C(O) R, $C(O)CH_2C(O)R$, C(S)R, C(O)OR, OC(O)R, C(O)N $(R)_2$, $OC(O)N(R)_2$, $C(S)N(R)_2$, $(CH_2)_{0-2}N(R)C(O)R$, $(CH_2)_{0-2}N(R)N(R)_2$, $N(R)N(R)C(O)R$, $N(R)N(R)C(O)$ OR, $N(R)N(R)CON(R)_2$, $N(R)SO_2R$, $N(R)SO_2N(R)_2$, N(R)C(O)OR, N(R)C(O)R, N(R)C(S)R, N(R)C(O)N $(R)_2$, $N(R)C(S)N(R)_2$, N(COR)COR, N(OR)R, $C(=NH)N(R)_2$, C(O)N(OR)R, and C(=NOR)R.

In certain embodiments, the mixture of a —$CHR^7CHR^8$— group, at least one —$CHR^7CHR^8$—$CHR^9$—OH group, or at least one —$CHR^7$—$NHR^8$ group referred to herein is present in a single substrate. In certain embodiments, the mixture of a —$CHR^7CHR^8$— group, at least one —$CHR^7CHR^8$—$CHR^9$—OH group, or at least one —$CHR^7$—$NHR^8$ group referred to herein is present in multiple substrates In certain embodiments, the compound of Formula (I) is a compound of Formula (II).

In some embodiments, at least one of $R^7$ and $R^{μ\ 8}$ is not hydrogen. In other embodiments, at least one of $R^7$, $R^8$, and $R^9$ is not hydrogen. In one embodiment, $R^7$, $R^8$, and $R^9$ are each independently H or $C_{1-30}$ hydrocarbyl. In various embodiments, $R^1$ is H. In various embodiments, $R^2$ is $CH_3$ or $CF_3$. In some embodiments, $R^4$ and $R^5$ are $CF_3$. In some embodiments, $R^3$ and $R^{3'}$ are $CH_3$.

The type of substrate used in the dehydrogenation described herein is not particularly limited, and can include compounds that already contain degrees of unsaturation between carbon-carbon bonds, alkanes, aldehydes, ketones, acids, esters, carbonates, amines, imines, amides, nitriles, sulfates, sulfones, and the like, as well as substrates that contain a mixture of these functional groups. The substrates can be cyclic, linear, branched, or combinations thereof. The compound of Formula I or Formula II can be present in catalytic amounts in the dehydrogenation reaction mixture. The compound of Formula I or Formula II can be present at a concentration of about $10^{-5}$ to about $10^{-1}$M, or about $10^{-4}$ to about $10^{-2}$M. In some embodiments, the catalytic amount of the compound of Formula I or Formula II can be present at a concentration of at least about, less than about, or greater than about $10^{-5}$, $10^{-4}$, $10^{-3}$, $10^{-2}$, or about $10^{-1}$M.

In some embodiments, the substrate includes a hydrocarbyl group. In some embodiments, the substrate is a $C_{2-30}$ hydrocarbon. In various embodiments, the substrate is selected from the group consisting of propane, butanes, pentanes, hexanes, heptanes, octanes, nonanes, decanes, undecanes, dodecanes, tetradecanes, hexadecanes, and mixtures thereof. In other embodiments, the substrate comprises at least one of ethane, propane, butane, or pentane, or combinations thereof. As used herein, in some embodiments, the plural forms of hydrocarbons such as "decanes" or "hexanes" includes at least one isomer of the parent hydrocarbon and/or the parent hydrocarbon itself. For example, "decanes" means at least one isomer of decane and/or decane itself. Similarly, "hexanes" means at least one isomer of hexane and/or hexane itself.

The compounds of Formula I or Formula II can be loaded onto a solid support. Suitable solid supports can be metal oxides such as zirconium dioxide, zinc oxide, aluminum oxide, silicon dioxide, titanium dioxide, magnesium oxide, lanthanum oxide, cerium oxide and mixtures thereof. Suitable solid supports further comprise aluminosilicates, including but not limited to $Al_2SiO_5$. In various embodiments, the solid support can be $SiO_2$, $Al_2O_3$, aluminosilicates, $ZrO_2$, or $TiO_2$. Suitable aluminosilicates include, but are not limited to, zeolites, clays, silicoaluminophosphates, and metal-organic frameworks.

The dehydrogenation can take place in a suitable dehydrogenation reactor that contains one or more feeds of substrate(s) to be dehydrogenated while allowing dihydrogen to escape from the system. The dehydrogenation can take place at a temperature of about 150° C. to about 600° C. or about 150° C. to about 350° C. In various embodiments, the dehydrogenation can take place at a temperature of at least about, greater than about, or less than about 150, 200 250, 300, 350, 400, 450, 500, 550, or about 600° C.

The pressure at which the dehydrogenation is conducted can be about 0.5 atm to about 5 atm, or about 1 atm to about 3 atm. In various embodiments, the dehydrogenation is conducted at a pressure of about 0.5, 0.75, 1, 1.5, 2, 2.5, 3, 3.5, 4, 4.5, or 5 atm.

Hydrogen gas produced during the dehydrogenation can be removed from the reaction vessel or chamber to drive the reaction further to completion and to increase yields of dehydrogenated substrates. The hydrogen gas can be purged from the reaction vessel and safely vented, or the hydrogen gas can be collected in a separate chamber for further use. Alternatively, the hydrogen can be removed via membranes such as proton-conducting membranes or hydrogen permeable membranes such as gallium, palladium, Pd-Ag, or Pd-Cu membranes.

In certain embodiments, the method further includes separating the substrate from the dehydrogenated product. Separation can be accomplished used techniques known in the art, such as for example, distillation, chromatography, surface adsorption, passing through membranes, and the like. In certain embodiments, selective olefin removal can be achieved by allowing the reaction mixture (containing both alkanes and olefins) to pass through a solid sorbent, trapping the olefins on the solid and returning the alkanes back to a dehydrogenation chamber. Suitable sorbents for selective olefin removal include, but are not limited to, solid-supported $Ag^+$, such as $Ag^+$ supported on silica, alumina, zirconia, titania, and carbon.

In certain embodiments, both the hydrogen and the dehydrogenation product can be removed via means discussed herein to facilitate the dehydrogenation reaction.

In yet another embodiment, the method further comprises converting the dehydrogenated products generated from the dehydrogenation reaction herein to form at least one final product. The final products can be produced in a tandem reaction, such as reaction that occurs after the production of the dehydrogenated product. Alternatively, the final product can be produced in the same reaction vessel, reactor, or chamber, after the formation of the dehydrogenated product has run to completion or is stopped. The final product can, in some embodiments, include heavier olefins, jet or diesel fuels, lubricant basestocks, detergents, fibers, plastics, resins, and combinations thereof. Heavier olefins, in some embodiments, include olefins with greater than four carbons.

EXAMPLES

Various embodiments of the present application can be better understood by reference to the following Examples which are offered by way of illustration. The scope of the present application is not limited to the Examples given herein.

Example 1: σ-Bond Metathesis in Dehydrogenation

Iridium complex $1^{CF_3}$-Me bearing the electron-poor carboxylate ligand $CF_3COO^-$ was prepared and was found to undergo net σ-bond metathesis with mesitylene to give $1^{CF_3}$-Mes at 100° C. It has previously been reported that Na$^+$ can catalyze a net M—H/C—H σ-bond metathesis. In the presence of Na[BArF], $1^{CF_3}$-Me reacted underwent net σ-bond metathesis with mesitylene at only 70° C. on the same time scale as at 100° C. in the absence of Na+ Surprisingly the apparent regioselectivity was different in the Na$^+$-catalyzed reaction. Instead of complete conversion to the benzylic derivative $1^{CF_3}$-Mes, an approximately 1:1 ratio of $1^{CF_3}$-Mes and the product of activation of an aryl C—H bond, $1^{CF_3}$-ArMe$_3$, was observed.

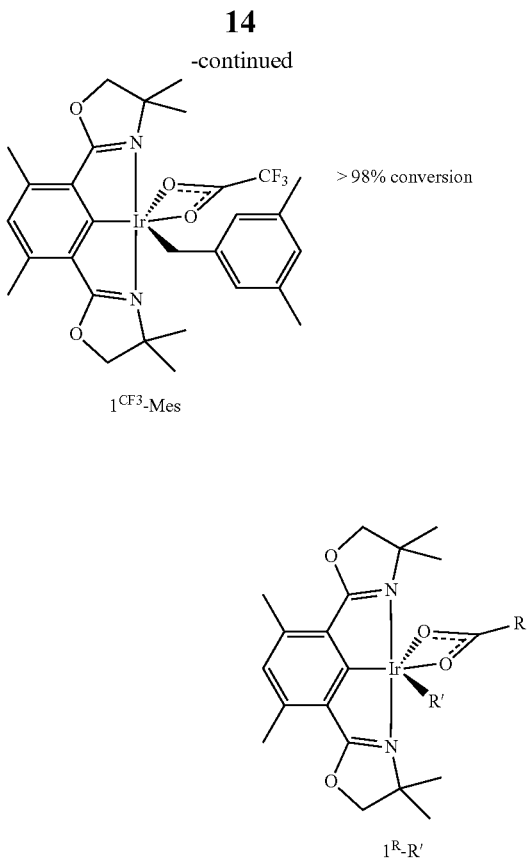

Scheme 1. σ-bond metathesis reactions (catalyzed and uncatalyzed) of 1-Me with mesitylene

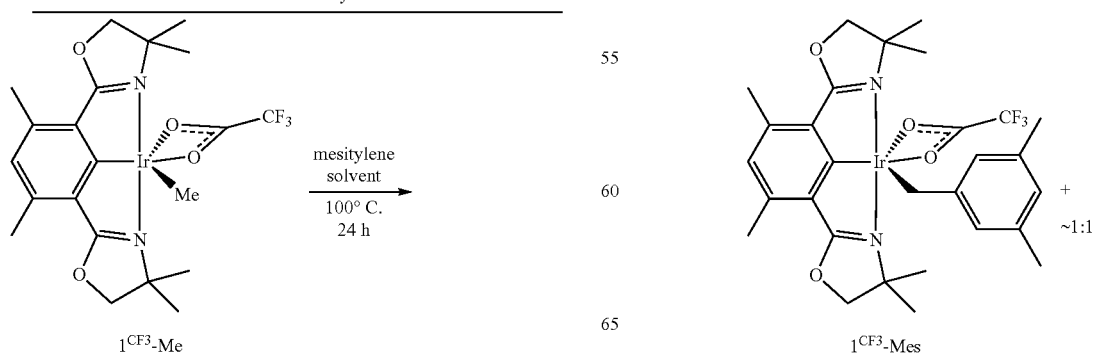

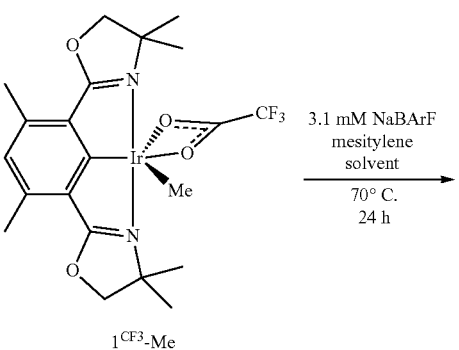

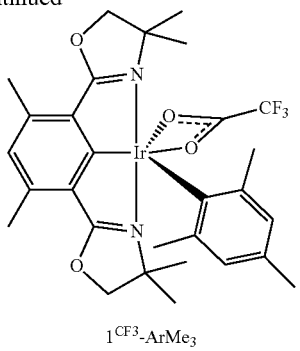

$1^{CF3}$-ArMe$_3$

The observed activity of $1^{CF3}$-H as an acceptorless dehydrogenation catalyst is not high. Using a standard protocol for acceptorless dehydrogenation (refluxing a solution of catalyst with an argon flow over the condenser to allow escape of H$_2$) an n-dodecane solution of $1^{CF3}$-H (1 mM) (b. p. 216° C., 250° C. oil bath) and 0.45 mM NaBArF as co-catalyst afforded only 6 mM decenes (6 turnovers (TO) based on iridium) after 24 h. Derivatives of $1^{CF3}$-H with various carboxylate ligands were prepared in quantitative yield by exchanging $1^{CF3}$-H with 1 eq of corresponding carboxylic acid, RCO$_2$H. However, all such complexes (1.0 mM 0.45 mM NaBArF) are also relatively poor catalysts for acceptorless dehydrogenation of n-dodecane, with less than 10 TO after 24 h under the same conditions (Scheme 2). Without being bound by theory, it is believed that rapid catalyst decomposition at the high reaction temperature is a significant factor in the low catalyst turnover numbers.

Scheme 2. Acceptorless dehydrogenation of n-dodecane by $1^R$-H and NaBArF

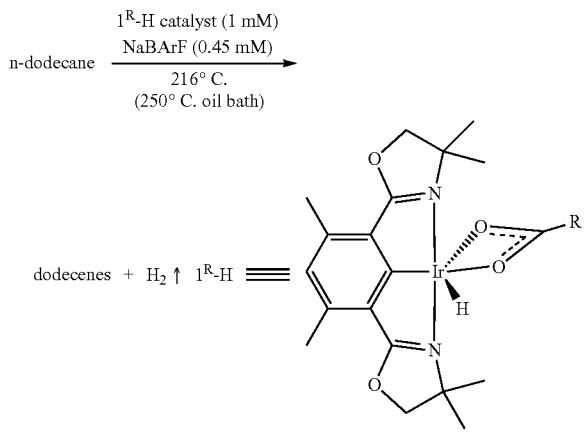

R = CF$_3$, C$_6$F$_5$, 3,5-C$_6$H$_3$(CF$_3$)$_2$, t-Bu

Example 2: Dehydrogenation with Compounds of Formula I

Surprisingly it was discovered that substituting methyl groups on the aryl ring of the ligand with CF$_3$ groups resulted in a more stable catalyst system. Moreover, the complex bearing CF$_3$ groups is expected to engender a more electrophilic metal center, which can, in some embodiments, facilitate the rate-determining C—H activation.

Development of a new metalation method was important to metalate the $^{CF3}$Phebox ligand described herein (Scheme 3). The use of conventional iridium precursors for iridium complexes such as IrCl$_3$.nH$_2$O or (COD)IrCl was unsuccessful. First, the $^{CF3}$Phebox was reacted with (COD)Ir (OAc) (OAc=CH$_3$C(=O)O) dimer at 180° C. to afford what appeared to be a mixture of ($^{CF3}$Phebox)Ir(R)(OAc). Continued heating at 180° C. with addition of i-PrOH generated ($^{CF3}$Phebox)Ir(H)(OAc) (Me$_2$-2-H). This general procedure can be used to synthesize other compounds of Formula II.

Scheme 3. Metalation of $^{CF3}$Phebox ligand

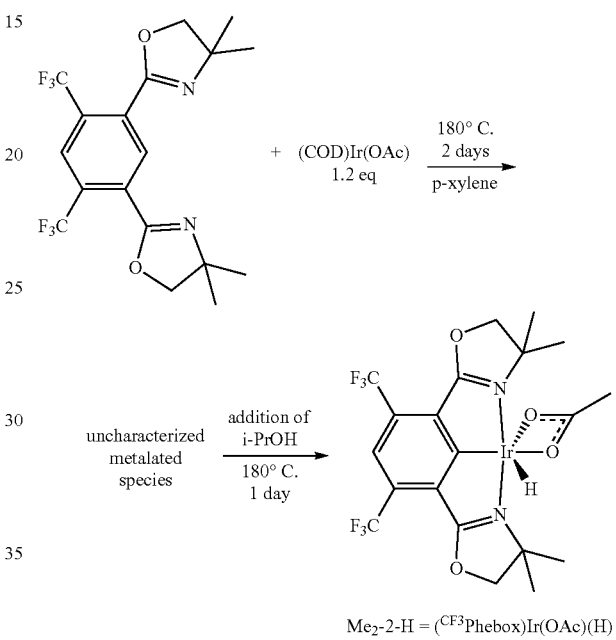

Me$_2$-2-H = ($^{CF3}$Phebox)Ir(OAc)(H)

Acceptorless dehydrogenation of n-dodecane by Me$_2$-2-H (0.5 mM) gave 123 mM dodecene after 48 h (Scheme 4). Additionally, 102 mM and 104 mM dodecene were obtained with 0.5 mM (CH$_2$)$_4$-2-H or (CH$_2$)$_5$-2-H respectively after 48 h.

Scheme 4. Acceptorless dehydrogenation of n-dodecane by R-2-H (R = Me$_2$, (CH$_2$)$_4$, (CH$_2$)$_5$)

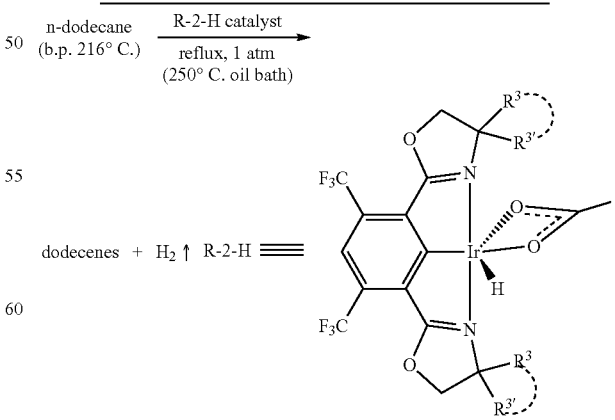

R$^3$, R$^{3'}$ = Me, Me; -(CH$_2$)$_4$-, -(CH$_2$)$_5$-

Reactions with various loadings of Me$_2$-2-H (0.25 mM, 0.5 mM, 1.0 mM) showed very similar curves for product concentration vs. time (FIG. 1). FIG. 1 suggests that the catalyst, in some embodiments, achieves an equilibrium between olefin, alkane, and H$_2$ in solution, and the observed rate is therefore limited by the rate of H$_2$ expulsion from solution under such conditions. At least 1180 TOs dodecene can be obtained using 0.05 mM Me$_2$-2-H after 24 h reflux, and 1420 TOs are obtained at 72 h.

For dehydrogenation of n-decane (b.p. 174° C.) (Scheme 5), the three R-2-H catalysts showed similar activity, with 16-19 mM decene detected after 24 h heating and ~40 mM decenes after 72 h (73 mM after 252 h by 0.5 mM Me$_2$-2-H), with an oil bath temperature of 210° C. With 0.5 mM NaBArF as co-catalyst, reaction curves with various concentration of Me$_2$-2-H (0.1 mM, 0.25 mM, 0.5 mM) are similar which suggests the reaction rate is limited by the rate of H$_2$ expulsion from solution. At least 240 TOs decene were obtained combining 0.1 mM cat. and 0.5 mM NaBArF after refluxing 24 h.

Scheme 5. Acceptorless dehydrogenation of n-decane by R-2-H

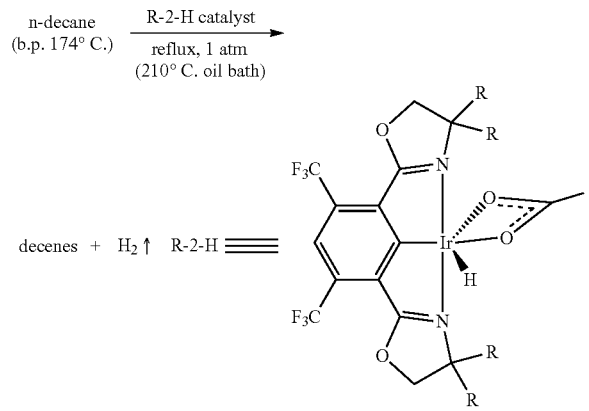

Example 3: Olefin Oligomerization with Simulated Dehydrogenation Mixture Derived from Compounds of Formula I To determine the effectiveness of olefin oligomerization of streams derived from dehydrogenation catalysis using compounds of formula I, model oligomerization reactions with 150 mM olefin in alkane were conducted. In a 4-mL Schlenk flask with a screw-cap, Amberlyst 15 Hydrogen catalyst was loaded along with 2 mL of 150 mM 1-octene in n-decane. 1-Octene oligomerization catalyzed by Amberlyst 15 Hydrogen was then conducted with the reaction temperature increased gradually from 100° C. to 120° C. to 150° C., which resulted 69% octene conversion and 22 mM C$_{16}$ as a broad peak in the GC (m/z$^+$224 by GC/MS).

Example 4: Tandem Alkane Dehydrogenation and Olefin Oligomerization

A two-pot reactor was employed in the tandem alkane dehydrogenation and olefin oligomerization described herein. 1.0 mM of a compound of formula I (($^{CF3}$Phebox) Ir(H)(OAc) (Me$_2$-2-H)) in dodecane was loaded in the first pot heated with an oil bath held at 280° C. The vapor from the first pot was allowed to condense to a second pot loaded with 10 mg of Amberlyst 15 and held at 120° C., before the liquid was allowed to return to the first pot. After two days of refluxing, 75 mM dodecenes and traces of C$_{12}$ dimer (<1 mM) were detected by GC and GC-MS.

Scheme 6. Tandem alkane dehydrogenation and olefin oligomerization

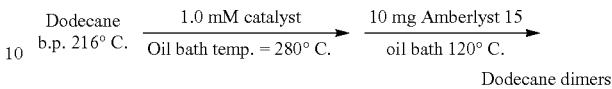

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Enumerated Embodiments

The following exemplary embodiments are provided, the numbering of which is not to be construed as designating levels of importance:

Embodiment 1 provides a compound of Formula I:

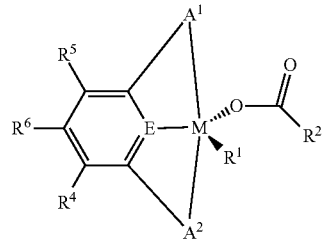

Formula I wherein:
M is a transition metal;
E is C or N;
R$^1$ is H or C$_{1-16}$ alkyl;
R$^2$ is selected from the group consisting of CH$_{3-m}$X$_m$, CF$_2$CF$_3$, C$_{6-14}$ aryl, and C$_{1-16}$ alkyl,
wherein the C$_{6-14}$ aryl and C$_{1-16}$ alkyl are each optionally substituted by at least one substituent independently selected from the group consisting of F, Cl, Br, I, OR, OC(O)N(R)$_2$, CN, NO, NO$_2$, ONO$_2$, azido, CF$_3$, OCF$_3$, R, C(O), S(O), methylenedioxy, ethylenedioxy, N(R)$_2$, SR, SOR, SO$_2$R, SO$_2$N(R)$_2$, SO$_3$R, C(O)R, C(O)C(O) R, C(O)CH$_2$C(O)R, C(S)R, C(O)OR, OC(O)R, C(O)N (R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O) OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N (R)$_2$, N(R)C(S)N(R)$_2$, N(COR)COR, N(OR)R, C(=NH)N(R)$_2$, C(O)N(OR)R, and C(=NOR)R; and each occurrence of R is independently at each occurrence H or $C_{1-16}$ hydrocarbyl;

each occurrence of X is independently selected from the group of H, F, Cl, and Br;

$A^1$ and $A^2$ are moieties that each comprise at least one nitrogen atom coordinated to M;

$R^4$ is selected from the group consisting of $CF_3$, $CF_2CF_3$, CN, and $NO_2$;

$R^5$ is selected from the group consisting of $CF_3$, $CF_2CF_3$, CN, and $NO_2$;

$R^6$ is independently selected from the group consisting of H, $CF_3$, $CF_2CF_3$, CN, and $NO_2$; and each occurrence of m is independently 0, 1, 2, or 3.

Embodiment 2 provides the compound of Embodiment 1, having the structure of Formula II:

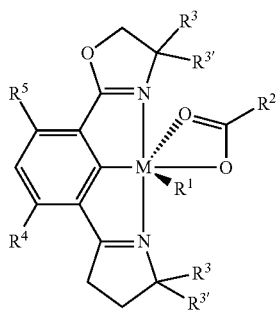

Formula II wherein $R^3$ and $R^{3'}$ are each $CH_3$, or $R^3$ and $R^{3'}$ taken together are —$(CH_2)_4$— or —$(CH_2)_5$—.

Embodiment 3 provides the compound of any one of Embodiments 1-2, wherein M is Co, Rh, Ru, or Ir.

Embodiment 4 provides the compound of any one of Embodiments 1-3, wherein M is Ir.

Embodiment 5 provides the compound of any one of Embodiments 1-4, wherein $R^1$ is H.

Embodiment 6 provides the compound of any one of embodiments 1-5, wherein $R^2$ is $CH_3$.

Embodiment 7 provides the compound of any one of embodiments 1-6, wherein $R^2$ is $CF_3$.

Embodiment 8 provides the compound of any one of embodiments 1-7, wherein $R^3$ and $R^{3'}$ are $CH_3$.

Embodiment 9 provides the compound of any one of embodiments 1-8, wherein $R^4$ and $R^5$ are $CF_3$.

Embodiment 10 provides the compound of any one of Embodiments 1-9, wherein $R^2$ is

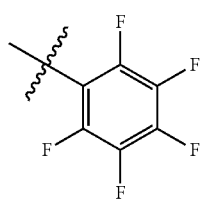 [SMILES: *c1c(F)c(F)c(F)c(F)c1F]

or

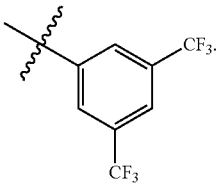

Embodiment 11 provides a method of dehydrogenating a substrate, the method comprising:

contacting at least one substrate comprising at least one moiety selected from the group consisting of —$CHR^7CHR^8$—, —$CHR^7CHR^8$—$CHR^9$—OH, —CHR'—$NHR^8$, and mixtures thereof with the compound of claim 1; and forming a corresponding dehydrogenated product from the substrate, wherein $R^7$, $R^8$, $R^9$ are each independently selected from the group consisting of H, F, Cl, Br, I, OR, OC(O)N(R)$_2$, CN, NO, $NO_2$, $ONO_2$, azido, $CF_3$, $OCF_3$, R, C(O), S(O), methylenedioxy, ethylenedioxy, N(R)$_2$, SR, SOR, $SO_2R$, $SO_2N(R)_2$, $SO_3R$, C(O)R, C(O)C(O)R, C(O)$CH_2$C(O)R, C(S)R, C(O)OR, OC(O)R, C(O)N(R)$_2$, OC(O)N(R)$_2$, C(S)N(R)$_2$, $(CH_2)_{0-2}N(R)C(O)R$, $(CH_2)_{0-2}N(R)N(R)_2$, N(R)N(R)C(O)R, N(R)N(R)C(O)OR, N(R)N(R)CON(R)$_2$, N(R)$SO_2R$, N(R)$SO_2N(R)_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R.

Embodiment 12 provides the method of embodiment 11, wherein the substrate comprises a hydrocarbyl group.

Embodiment 13 provides the method of any one of embodiments 11-12, wherein the substrate is selected from the group consisting of propane, butanes, pentanes, hexanes, heptanes, octanes, nonanes, decanes, undecanes, dodecanes, tetradecanes, hexadecanes, and mixtures thereof.

Embodiment 14 provides the method of any one of embodiments 11-13, wherein the compound of claim 1 is loaded onto a solid support.

Embodiment 15 provides the method of any one of embodiments 11-14, wherein the solid support comprises $SiO_2$, $Al_2O_3$, aluminosilicate, $ZrO_2$, or $TiO_2$.

Embodiment 16 provides the method of any one of embodiments 11-15, further comprising separating the substrate from the dehydrogenated product.

Embodiment 17 provides the method of any one of embodiments 11-16, wherein $R^1$ is H.

Embodiment 18 provides the method of any one of embodiments 11-17, wherein $R^2$ is $CH_3$.

Embodiment 19 provides the method of any one of embodiments 11-18, wherein $R^2$ is $CF_3$.

Embodiment 20 provides the method of any one of embodiments 11-19, wherein $R^4$ and $R^5$ are $CF_3$.

Embodiment 21 provides the method of any one of embodiments 11-20, wherein $R^3$ and $R^{3'}$ are $CH_3$.

Embodiment 22 provides the method of any one of embodiments 11-21, further comprising converting the dehydrogenated product to a final product.

Embodiment 23 provides the method of embodiment 22, wherein the converting comprises olefin oligomerization.

Embodiment 24 provides the method of any one of embodiments 22-23, wherein the final product comprises at least one of a heavier olefin, jet or diesel fuel, lubricant basestock, detergent, fiber, plastic, resins, or combinations thereof.

Embodiment 25 provides the method of any one of embodiments 11-24, wherein $R^7$, $R^8$, and $R^9$ are not all hydrogen at the same time.

Embodiment 26 provides the method of any one of embodiments 11-25, wherein $R^7$, $R^8$, and $R^9$ are each independently H or $C_{1-30}$ hydrocarbyl.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A compound of Formula I:

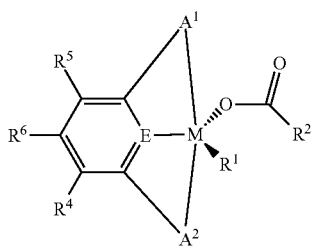

Formula I wherein:

M is a transition metal;

E is C or N;

1e is H or $C_{1-16}$ alkyl;

$R^2$ is selected from the group consisting of $CH_{3-m}X_m$, $CF_2CF_3$, $C_{6-14}$ aryl, and $C_{1-16}$ alkyl, wherein the $C_{6-14}$ aryl and $C_{1-16}$ alkyl are each optionally substituted by at least one substituent independently selected from the group consisting of F, Cl, Br, I, OR, OC(O)N(R)$_2$, CN, NO, NO$_2$, ONO$_2$, azido, CF$_3$, OCF$_3$, R, C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C($=$NH)N(R)$_2$, C(O)N(OR)R, and C($=$NOR)R; and each occurrence of R is independently at each occurrence H or $C_{1-16}$ hydrocarbyl;

each occurrence of X is independently selected from the group of H, F, Cl, and Br;

$A^1$ and $A^2$ are moieties that each comprise at least one nitrogen atom coordinated to M;

$R^4$ is selected from the group consisting of CF$_3$, CF$_2$CF$_3$, CN, and NO$_2$;

$R^5$ is selected from the group consisting of CF$_3$, CF$_2$CF$_3$, CN, and NO$_2$;

$R^6$ is independently selected from the group consisting of H, CF$_3$, CF$_2$CF$_3$, CN, and NO$_2$; and each occurrence of m is independently 0, 1, 2, or 3.

2. The compound of claim 1, having the structure of Formula II:

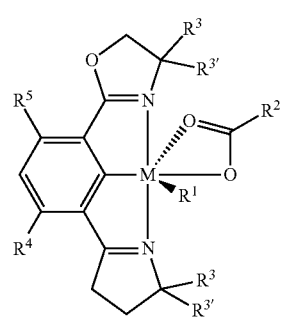

Formula II wherein $R^3$ and $R^{3'}$ are each CH$_3$, or $R^3$ and $R^{3'}$ taken together are —(CH$_2$)$_4$— or —(CH$_2$)$_5$—.

3. The compound of claim 1, wherein M is selected from the group consisting of Co, Rh, Ru, and Ir.

4. The compound of claim 3, wherein M is Ir.

5. The compound of claim 1, wherein $R^1$ is H.

6. The compound of claim 1, wherein $R^2$ is selected from the group consisting of CF$_3$, CH$_3$,

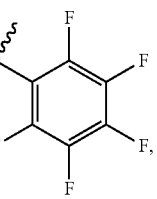

and

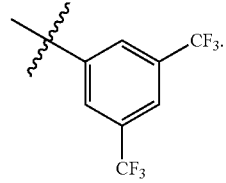 [SMILES: *c1cc(C(F)(F)F)cc(C(F)(F)F)c1]

7. The compound of claim 2, wherein $R^3$ and $R^{3'}$ are CH$_3$.

8. The compound of claim 1, wherein $R^4$ and $R^5$ are CF$_3$.

9. The compound of claim 1, wherein $R^4$ and $R^5$ are CF$_2$CF$_3$.

10. The compound of claim 1, wherein the $C_{6-14}$ aryl is $C_6F_5$ or 3,5-diCF$_3$—C$_6$H$_3$.

11. A method of dehydrogenating a substrate, the method comprising:

contacting at least one substrate comprising at least one moiety selected from the group consisting of —CHR$^7$CHR$^8$—, —CHR$^7$CHR$^8$—CHR$^9$—OH, —CHR'—NHR$^8$, and mixtures thereof with a compound of Formula I:

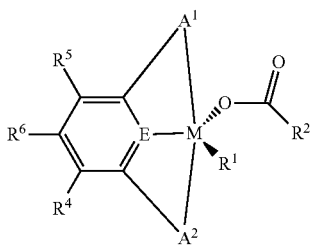

Formula I wherein:
M is a transition metal;
E is C or N;
$R^1$ is H or $C_{1-16}$ alkyl;
$R^2$ is selected from the group consisting of $CH_{3-m}X_m$, $CF_2CF_3$, $C_{6-14}$ aryl, and $C_{1-16}$ alkyl,
  wherein the $C_{6-14}$ aryl and $C_{1-16}$ alkyl are each optionally substituted by at least one substituent independently selected from the group consisting of F, Cl, Br, I, OR, OC(O)N(R)$_2$, CN, NO, NO$_2$, ONO$_2$, azido, CF$_3$, OCF$_3$, R, C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R; and
  each occurrence of R is independently at each occurrence H or $C_{1-16}$ hydrocarbyl;
each occurrence of X is independently selected from the group of H, F, Cl, and Br;
$A^1$ and $A^2$ are moieties that each comprise at least one nitrogen atom coordinated to M;
$R^4$ is selected from the group consisting of CF$_3$, CF$_2$CF$_3$, CN, and NO$_2$;
$R^5$ is selected from the group consisting of CF$_3$, CF$_2$CF$_3$, CN, and NO$_2$;
$R^6$ is independently selected from the group consisting of H, CF$_3$, CF$_2$CF$_3$, CN, and NO$_2$; and
each occurrence of m is independently 0, 1, 2, or 3;
forming a corresponding dehydrogenated product from the substrate; and
optionally further comprising separating the substrate from the dehydrogenated product,
wherein $R^7$, $R^8$, $R^9$ are each independently selected from the group consisting of H, F, Cl, Br, I, OR, OC(O)N(R)$_2$, CN, NO, NO$_2$, ONO$_2$, azido, CF$_3$, OCF$_3$, R, C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R.

12. The method of claim 11, wherein the substrate comprises a hydrocarbyl group.

13. The method of claim 11, wherein the substrate is selected from the group consisting of propane, butanes, pentanes, hexanes, heptanes, octanes, nonanes, decanes, undecanes, dodecanes, tetradecanes, hexadecanes, and mixtures thereof.

14. The method of claim 11, wherein the compound of Formula I is loaded onto a solid support.

15. The method of claim 14, wherein the solid support comprises SiO$_2$, Al$_2$O$_3$, aluminosilicates, ZrO$_2$, or TiO$_2$.

16. The method of claim 11, further comprising separating the substrate from the dehydrogenated product.

17. The method of claim 11, wherein $R^1$ is H.

18. The method of claim 11, wherein $R^2$ is CH$_3$.

19. The method of claim 11, wherein $R^2$ is CF$_3$.

20. The method of claim 11, wherein $R^4$ and $R^5$ are CF$_3$.

21. The method of claim 11, wherein the compound of Formula I is a compound of Formula II:

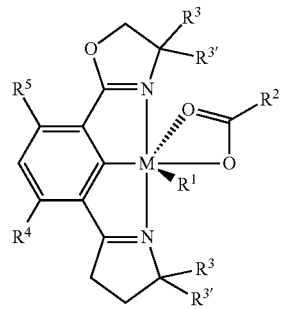

Formula II wherein $R^3$ and $R^{3'}$ are each CH$_3$, or $R^3$ and $R^{3'}$ taken together are —(CH$_2$)$_4$— or —(CH$_2$)$_5$—.

22. The method of claim 11, further comprising converting the dehydrogenated product to a final product.

23. The method of claim 22, wherein the converting comprises olefin oligomerization.

24. The method of claim 22, wherein the final product comprises at least one of a heavier olefin, jet or diesel fuel, lubricant basestock, detergent, fiber, plastic, resins, or combinations thereof.

25. The method of claim 11, wherein at least one of $R^7$, $R^8$, and $R^9$ is not hydrogen.

26. The method of claim 25, wherein $R^7$, $R^8$, and $R^9$ are each independently H or $C_{1-30}$ hydrocarbyl.

27. The method of claim 21, wherein $R^3$ and $R^{3'}$ are CH$_3$.

* * * * *